(12) United States Patent
Koch

(10) Patent No.: US 6,610,481 B2
(45) Date of Patent: *Aug. 26, 2003

(54) CASCADE NUCLEIC ACID AMPLIFICATION REACTION

(76) Inventor: Jørn Erland Koch, Vittenvej 124, Hinnerup DK-8382 (DK)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/465,589

(22) Filed: Dec. 17, 1999

(65) Prior Publication Data

US 2002/0031764 A1 Mar. 14, 2002

Related U.S. Application Data

(62) Division of application No. 09/091,146, filed as application No. PCT/DK96/00513 on Dec. 5, 1996, now abandoned.

(30) Foreign Application Priority Data

Dec. 5, 1995 (DK) .............................. 1379/95

(51) Int. Cl.⁷ .......................... C12Q 1/68; C12P 19/34; C07H 21/00
(52) U.S. Cl. ....................... 435/6; 435/91.2; 435/91.51; 435/91.52; 536/22.1
(58) Field of Search ............................. 435/91.2, 91.51, 435/91.52; 536/22.1

(56) References Cited

U.S. PATENT DOCUMENTS

| | | | |
|---|---|---|---|
| 4,683,195 A | 7/1987 | Mullis | 435/6 |
| 4,683,202 A | 7/1987 | Mullis | 435/91 |
| 4,800,159 A | 1/1989 | Mullis | 435/172.3 |
| 5,854,033 A | 12/1998 | Lizardi | 435/91.2 |
| 5,876,924 A | 3/1999 | Zhang et al. | 435/5 |
| 5,942,391 A | 8/1999 | Zhang et al. | 435/6 |

FOREIGN PATENT DOCUMENTS

| | | | |
|---|---|---|---|
| EP | 0 497 272 | 8/1992 | |
| EP | 0 500 224 | 8/1992 | |
| EP | 0 543 612 | 5/1993 | |
| JP | 4262799 | 9/1982 | |
| JP | 04304900 | 10/1992 | ............ C12Q/1/68 |
| WO | 92/01813 | * 2/1992 | ............ C12Q/1/68 |
| WO | WO 92/01813 | 2/1992 | ............ C12Q/1/68 |
| WO | WO 93/04198 | 3/1993 | |
| WO | WO 93/09245 | 5/1993 | ............ C12P/19/34 |
| WO | WO 94/03630 | 2/1994 | ............ C12Q/1/68 |
| WO | WO 95/35390 | 12/1995 | ............ C12Q/1/68 |
| WO | WO 97/19193 | 5/1997 | |

OTHER PUBLICATIONS

Andrew Fire and Si–Qun Xu, "Rolling replication of short DNA circles," *Proc. Natl. Acad. Sci. USA 92,* May 1995, vol. 92, pp. 4641–4645.

Michael J. White et al. "Concatemer Chain Reaction: A Taq DNA Polymerase–Mediated Mechanism for Generation Long Tandemly Repetitive DNA Sequences," *Analytical Biochemistry,* Dec. 1991, vol. 199, No. 2, pp. 184–190.

* cited by examiner

*Primary Examiner*—Jeffrey Siew
*Assistant Examiner*—Joyce Tung
(74) *Attorney, Agent, or Firm*—Darby & Darby

(57) ABSTRACT

A process for generating multiple linear complements of a single strand, circular nucleic acid template containing at least one cleavage site is described. The process consists of combining the single strand, circular nucleic acid template with polynucleotide primers under conditions sufficient for hybridization; extending the polynucleotide primer more than once around the circle to generate a complementary displacement of more than one contiguous complement of the single strand, circular nucleic acid template. Also described is a process of synthesizing novel single strand, circular nucleic acids between 30 an 2200 nucleotides. The process consist of synthesizing a linear polynucleotide; combining the linear polynucleotide with a complementary linking oligonucleotide under conditions sufficient for hybridization; and ligating the linear polynucleotide pto produce a single strand, circular nucleic acid.

22 Claims, 6 Drawing Sheets

Fig. 1  One dyad symmetry oligonucleotide:

Perfect match:   5'GAAATTTCGAAATTTC 3'
                 3' CTTTAAAGCTTTAAAG 5'

Frame-shift:
```
         5'                        3'   DNA synthesis
            GAAATTTCGAAATTTC       →
                    ←  3' CTTTAAAGCTTTAAAG 5'
    DNA synthesis
```

After frameshift and DNA synthesis:

```
  5'                              3'
     GAAATTTCGAAATTTCGAAATTTC
     CTTTAAAGCTTTAAAGCTTTAAAG
  3'                              5'
```

Fig. 2  Two complementary oligonucleotides:

Perfect match:
```
  5'GAAAGAAAGAAAGAAAGAAA3'
  3'CTTTCTTTCTTTCTTTCTTT5'
```

Frame-shift:
```
                                    DNA synthesis
      5'                         3'
         GAAAGAAAGAAAGAAAGAAA       →
                ← CTTTCTTTCTTTCTTTCTTT
                3'                      5'
  DNA synthesis
```

After frameshift and DNA synthesis:
```
  5'GAAAGAAAGAAAGAAAGAAAGAAAGAAA3'
    CTTTCTTTCTTTCTTTCTTTCTTTCTTT
  3'                           5'
```

Fig. 3  Co-amplification of the sequence:
NNNNNNNNNNNN
↓ Frameshifted annealing    and DNA synthesis
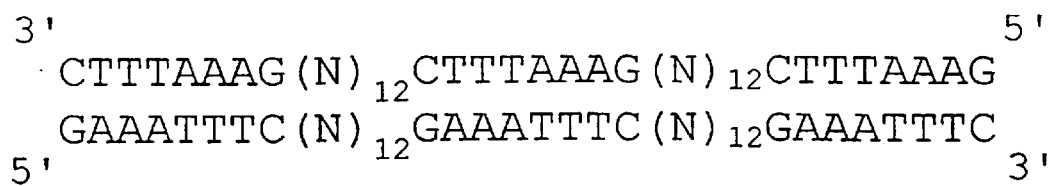

Fig. 4
(1)
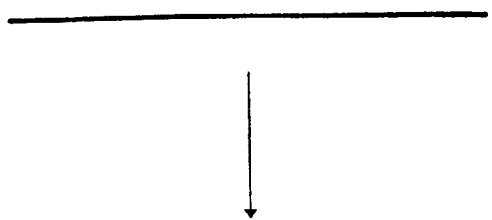
(2)
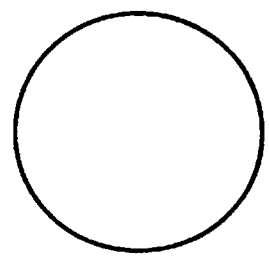
(3)
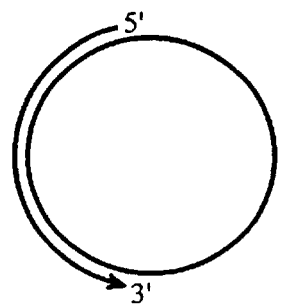
(4)
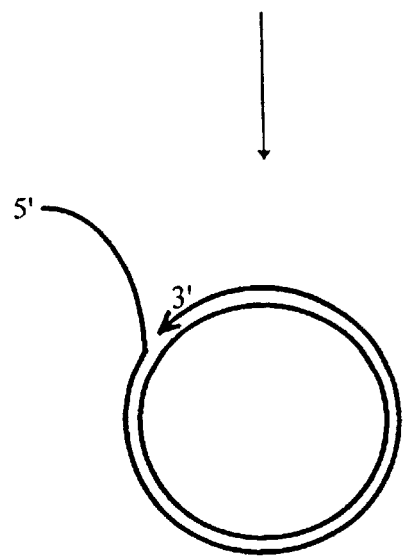

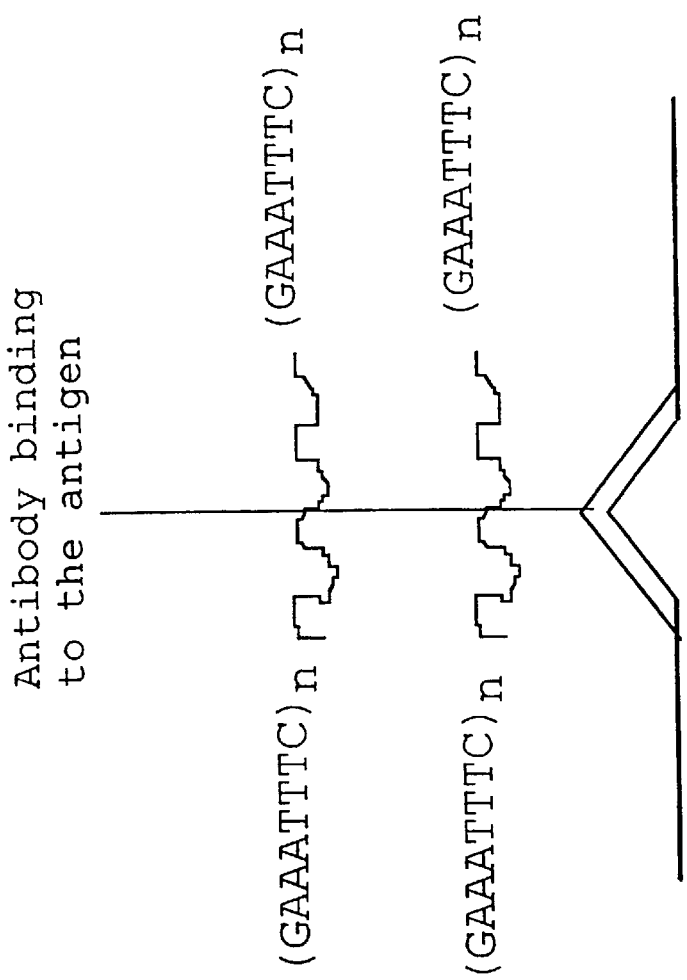
Fig. 6  Dyad symmetry oligonucleotides attached to an antibody for subsequent cascade reaction at the site of antibody binding

CASCADE NUCLEIC ACID AMPLIFICATION REACTION

This is a divisional of application Ser. No. 09/091,146, filed Jun. 4, 1998, now abandoned, which is the U.S. National Phase of International Appln. No. PCT/DK96/00513, filed Dec. 5, 1996. The most recent of these prior applications is hereby incorporated herein by reference, in its entirety.

This invention relates to a process of producing DNA consisting of multiple tandem repetitions of an oligonucleotide unit and a cascade nucleic acid amplification reaction producing a great number of partial and complete DNA or RNA copies thereof. The invention also relates to the application of these reactions in a method of detecting a target molecule or group at a specific site and a process for the amplification of a particular DNA sequence.

BACKGROUND OF THE INVENTION

The well-known polymerase chain reaction (PCR) is a process for amplifying any specific nucleic acid sequence contained in a nucleic acid or mixture of nucleic acids. In general, the process involves a chain reaction for producing, in exponential quantities relative to the number of reaction steps involved, any specific nucleic acid sequence given (a) that the ends of the sequence are known in sufficient detail that two oligonucleotide primers can be synthesized which will hybridize to them, and (b) that a small amount of the sequence is available to initiate the chain reaction. The process comprises treating separate complementary strands of the nucleic acid with a molar excess of two oligonucleotide primers, and extending the primers in the presence of a nucleic acid polymerase and the four necessary nucleoside triphosphates to form complementary primer extension products which act as templates for synthesizing the specific nucleic acid sequence. When the complementary strands of the nucleic acid are separated, e.g. by heating, the strands are ready to be used as templates for the synthesis of complementary strands by primer extension thus doubling the number of copies of the specific nucleic acid sequence. The steps of strand separation and extension product synthesis can be repeated as often as needed to produce the desired quantity of the specific nucleic acid sequence. This basic process is described and claimed in U.S. Pat. No. 4,683,202, and variants thereof are described and claimed in the related U.S. Pat. Nos. 4,683,195 and 4,800,159.

Becton Dickinson has described a variant of the PCR technique where the thermocycling is replaced by an enzymatic destruction of the primers, thus freeing the target sequence originally binding the primer to make it able to bind a new primer (EP 0 497 272 A1, EP 0 500 224 A2, EP 0 543 612 A2). After binding of the second primer to the target sequence, the product generated by chain elongation from the first primer is removed by strand displacement as the second primer is elongated. Like PCR, this reaction employs primers annealing to both ends of a biological DNA molecule with the purpose of amplifying the intervening biological sequence. This is unlike the present DNA cascade which relies on primers annealing along the length of a constructed tandemly repeated sequence (referred to as "polymer").

Strand displacement is also involved in other DNA techniques such as the commonly used random priming labeling of hybridization probes. However, in this approach all DNA present can serve as template for the reaction. This is unlike the present DNA cascade, which is restricted to a specific pre-selected template.

PRINS reactions can also be enhanced by strand displacement DNA synthesis after destruction of already elongated primer, as described by this inventor and patented by Boehringer Mannheim. Like the Becton Dickinson reaction, this produces multiple copies of a biological target sequence, but does not have the characteristics of the present DNA cascade reaction.

J. W. IJdo et al., Nucleic Acids Research, Vol. 19, No. 17, p. 4780 (1991), report the rapid generation of human telomere repeat sequence $(TTAGGG)_n$, with fragment sizes up to 25 kb, using a technique related to the polymerase chain reaction (PCR). The reaction is carried out in the absence of template using primers $(TTAGGG)_5$ (SEQ ID NO:1) and $(CCCTAA)_5$ (SEQ ID NO:2). Staggered annealing of the primers provides a single strand template for extension by Taq polymerase. The primers serve as both primer and template in the early cycles, whereas the newly formed sequences serve as primer and template in subsequent stages of the reaction resulting in a heterogeneous population of molecules consisting of repeat arrays of various lengths.

The DNA synthesized is only used as a probe for hybridization, and the approach thus serves as an alternative to other procedures for labeling of hybridization probes (like end-labeling or tailing). Unlike the approach described here, no surplus short primer is added to the resulting polymers to release a cascade reaction.

A commonly used method for randomly amplifying human DNA is called alu-PCR. This approach utilizes the fact that the human genome contains certain interspersed repeated elements called alu-repeats. These closely similar elements are on the average found once every ca. 10 kb of human genomic DNA. Though the actual distance between two neighboring alu-elements differ significantly along the genome, most of these elements are situated close enough to their neighbors to enable amplification by PCR of the intervening non-alu sequence after hybridization of primers to the alu-sequence.

British Technology Group Ltd has described a similar approach for the detection of Bovine Encephalitis viruses by PCR (WO 9304198 A1). In this case the interspersed repeat is comprised of a tandemly repeated sequence containing six base monomers, each having a sequence exhibiting a dyad symmetry. It is consequently possible to amplify the intervening sequences using only one primer (binding to both strands) rather than the two primers normally employed in other types of PCR, such as the alu-PCR. The fact that the naturally occurring repeat, which is detected by this technique, holds a dyad symmetry entity, gives it a possible chance similarity to one variant of the polymer synthesized by the reactions described here. In such cases where the intervening sequences are sufficiently short, the bovine virus DNA should thus be able to serve as the template for a DNA cascade. However, such a possibility is not recognized in the British Technology Group Patent, which only refers to PCR as the resulting amplification reaction. The chance similarities also imply that both the bovine virus test and some variants of the DNA cascade make use of primers with a dyad symmetry. However, whereas these primers in the DNA cascade are used to construct a molecule, and work on the constructed molecule, the primers in the bovine encephalitis test are only thought of as probes for the diagnostic detection of certain naturally occurring DNA molecules.

In the Japanese unexamined Patent Application, publication no. 04-262799, belonging to Toyobo Co. Ltd., Toshiya & Yutaka have described the formation from a circular DNA molecule of a polymer like the one used as starting material for the present DNA cascade. They obtain the DNA circle by circularizing a designed linear DNA molecule onto a biological DNA molecule, using the circularization as a test for the presence of the relevant biological molecule. After circularization of the test molecule, they add a third DNA molecule capable of binding to the part of the test molecule that did not hybridize with the biological molecule. This third molecule then serves as a primer for rolling circle replication of the circularized test molecule, thus forming a tandem repeat polymer derived from this. In this approach it is not envisioned that the polymer thus generated could be used as the starting material for a DNA cascade. Neither is it suggested that the circularization process could be positioned at the 3'-end of the biological molecule, such that this end could be used as a primer for the rolling circle replication, eliminating the need for the addition of a third DNA molecule to prime this, nor that the reaction could be inverted, such that it is the biological molecule, which is circularized.

SUMMARY OF THE INVENTION

Till now, the very successful techniques for the enzymatic amplification of DNA have been designed to amplify nucleic acid sequences of biological origin to enable studies of or with these sequences. The present invention represents a new strategy, termed a "DNA cascade", which is to amplify synthetic DNA. The amplification on process may then secondarily be used as a marker in biological analyses, and to co-amplify nucleic acid sequences of biological origin.

The DNA cascade is a technique for the production of multiple partial or complete copies of a preformed template. This is obtained after the initial construction ("linear multiplication reaction", phase 1) of a suitable template which consists of multiple tandem repetitions of an oligonucleotide unit, each of which can per se serve as a specific starting point for the copying process (the "cascade amplification reaction", phase 2).

The template for the cascade reaction may be built from two complementary oligonucleotides with an internal repetition unit in a manner similar to that described by J.W. IJdo et al., loc. cit.

However, the template is most conveniently produced by a novel process according to the invention from one oligonucleotide comprising at least one and a halt and preferably two units of a nucleotide sequence showing dyad symmetry.

This process involves repeated denaturation and annealing events to enable the oligonucleotide to grow stepwise by primed synthesis catalyzed by a DNA polymerase in the presence of the necessary nucleoside triphosphates.

This repeated denaturation and annealing can be achieved by thermocycling as illustrated in example 1, but could also be achieved by other means. One possibility would be to incubate the oligonucleotide(s) at the melting point of their duplex form (or slightly above this temperature). This would result in a statistical equilibrium, where a fraction of the molecules at any given time could support chain elongation, and thus polymer growth. In such a setup the temperature cycling would be replaced by a temperature gradient forcing the molecules to become longer and longer to accommodate for the increasing incubation temperature. The advantage of the gradient approach is that it does not require incubations at high temperatures, especially not if the DNA sequences chosen are rich in adenine and thymine. The avoidance of high incubation temperatures may be of advantage if the polymer formation is performed while the oligonucleotides are attached to specific detection reagents like avidin or antibodies, as such molecules tolerate high temperatures poorly.

Thus, in a first aspect the present invention provides a process for producing DNA consisting of multiple tandem repetitions of an oligonucleotide unit, wherein an oligonucleotide comprising at least one and a half unit of a nucleotide sequence showing dyad symmetry is copied stepwise by means of a template- and primer-dependent DNA polymerase in the presence of the necessary nucleoside triphosphates during repeated cycles of denaturation and annealing, the chain elongation taking place each time the annealing results in a frame-shifted hybridization giving rise to duplexes with buried 3' ends.

The sequence of bases in the oligonucleotide could be freely chosen according to the individual needs, but in order to be able to participate in the polymerization process, the oligonucleotide must consist of at least one and a half copy of the sequence intended to be the repeating unit of the polymer. Furthermore, it may be desirable to construct the oligonucleotide such that it consists of repeats of a sequence showing dyad symmetry, since this makes the sequence complementary to itself and eliminates the need for the inclusion of a second (complementary) oligonucleotide in the polymerization process. Thus, the shortest repeating unit showing dyad symmetry would be two complementary bases, for instance the sequence "AT". One and a half unit of this sequence would be "ATA", and the shortest oligonucleotide able to serve as a substrate for the polymerization on its own would thus be a three base oligonucleotide like "ATA". Any repeating dyad symmetry unit larger than two bases and anyone number of dyad symmetry units larger than one and a half could also be chosen, the only limitation being the technical limitations on the size of the oligonucleotide imposed by the process used to produce the oligonucleotide. Preferably, the starting oligonucleotide comprises at least two units of the nucleotide sequence showing dyad symmetry.

In a particular embodiment of the process for producing the template the nucleotide sequence showing dyad symmetry comprises the promoter region for an enzyme capable of template-dependent DNA or RNA synthesis without the need for a primer and the complementary repeat of said region. The presence of such a promoter region in each oligonucleotide unit of the template may be of advantage in the carrying out of the subsequent cascade phase as explained below.

In another particular embodiment of the above process any nucleotide sequence to be amplified is inserted between the copies of the nucleotide sequence showing dyad symmetry in the starting oligonucleotide. If such inserted nucleotide sequence comprises the promoter region for an enzyme capable of template-dependent DNA or RNA synthesis without the need for a primer, the same result is obtained as in the first particular embodiment above.

A nucleic acid template consisting of multiple tandem repetitions of an oligonucleotide unit can also be produced by another novel process according to the invention which involves circularization of one oligonucleotide so that it has no end and thus can act as a template for an endless copying process catalyzed by an enzyme that displaces rather than digests DNA or RNA occupying the part of the circular oligonucleotide which it is about to copy producing a large molecule being a multimer of the oligonucleotide.

Thus, in a second aspect the present invention provides a process for producing nucleic acid consisting of multiple tandem repetitions of an oligonucleotide unit, wherein a circular oligonucleotide comprising at least one copy of said unit is used as a template for an endless copying process by means of a nucleic acid polymerase, which is capable of strand displacement and is substantially without 5'-3' exonuclease activity, in the presence of the necessary nucleoside triphosphates and, if necessary, a primer capable of binding to some portion of the oligonucleotide.

The circularization process can be of two kinds, as the reaction can be designed to circularize any of the two strands on the other. If using a synthetic sequence and a biological sequence, one could thus choose to circularize the biological sequence on the synthetic or the synthetic on the biological, all depending on the design of the experiment. Likewise, one could either circularize the strand to be circularized at the 3'-end of the template strand, such that this could serve also serve as primer for the polymer formation, or one could do the circularization away from the 3'-end of the template, such that the addition of a separate primer for the rolling circle replication would be necessary.

When a polymerase capable of template- and primer-dependent DNA or RNA synthesis is used, the copying is started from a primer binding to some portion of the circular oligonucleotide.

With a view to a subsequent cascade reaction the polymerase is preferably a template- and primer-dependent DNA polymerase, and it may be of advantage that the circular oligonucleotide comprises a DNA sequence showing dyad symmetry, and the primer has the same DNA sequence.

When a template-dependent RNA polymerase without the need for a primer is used, the copying is started from a promoter region incorporated in the circular oligonucleotide and being recognized by the polymerase.

In that case, if it is desired to carry out a subsequent cascade reaction, it is necessary to produce a DNA multimer from the resulting RNA multimer by means of a reverse transcriptase and a DNA primer.

For purposes of monitoring the linear multiplication reaction and detecting the multimer product it may be useful that the nucleoside triphosphates present are labeled. Such label can for example be an enzyme, a radioactive isotope, a fluorescent compound, a chemiluminescent compound, a bioluminescent compound, a metal chelate or a hapten detectable by a specific secondary reaction.

The cascade amplification reaction comprises a copying of the template in an enzyme catalyzed process that originates from multiple repeating units in the template, thus making it possible to produce multiple copies of any segment of the template. To obtain this it is necessary to use enzymes that displaces rather than digests DNA or RNA occupying the part of the template which it is about to copy. As the sequences of the produced copies are both identical and complementary, they are able to aggregate forming large complexes with a decreased mobility relative to the individual molecules.

Accordingly, in a second aspect the present invention provides a cascade nucleic acid amplification reaction, wherein a great number of partial and complete DNA or RNA copies of a DNA template consisting of multiple tandem repetitions of an oligonucleotide unit is produced by means of a nucleic acid polymerase, which is capable of strand displacement and is substantially without 5'-3' exonuclease activity, by contacting the template with said nucleic acid polymerase in the preserve of the necessary nucleoside triphosphates and, if necessary, a primer capable of binding to the oligonucleotide unit, the polymerase thus synthesizing DNA or RNA originating from, ideally, each repeating oligonucleotide unit in the template.

If any part of the repeating oligonucleotide unit corresponds to the promoter of an enzyme capable of template-dependent DNA or RNA synthesis without the need for a primer as a starting point for the process, like the T3, T7 or SP6 RNA polymerase, the cascade phase can be induced by the simple addition of this enzyme and the necessary nucleoside triphosphates to the single-stranded or double-stranded template, preferably the double-stranded template.

If this is not the case, a primer capable of binding to the repeating oligonucleotide unit is needed along with a suitable enzyme that can synthesize DNA or RNA from the appropriate nucleoside triphosphates in a template- and primer-dependent reaction and has the aforementioned ability to induce strand displacement. In this case the strands of the template must first be separated so that the primer is able to hybridize to each strand. Suitable DNA polymerases of this kind are e.g. the Klenow fragment of DNA polymerase I, preparations of the Taq polymerase without exonuclease activity or the T4 DNA polymerase.

If the DNA template is produced from a circular oligonucleotide by means of a DNA polymerase starting from a primer binding to some portion of the circular oligonucleotide, the cascade reaction may be carried out simultaneously with the template formation by adding a primer binding to at least a portion of the complementary oligonucleotide units comprising the template.

In this case, as mentioned previously, it is advantageous that the starting circular oligonucleotide comprises a DNA sequence showing dyad symmetry, and the primer has the same DNA sequence, as then both the template formation and the cascade reaction therefrom will take place using the same single primer.

When the nucleic acid polymerase is a DNA polymerase, the synthesized strands displaced from the template are also DNA, and the cascade reaction proceeds further from the repeated oligonucleotide units of the newly synthesized DNA strands.

In a particular embodiment of such a cascade reaction the time of conducting the cascade reaction is adjusted to the number of repeated units in the template and, possibly, the concentration of primer in such a way that the copying of the template and the newly synthesized DNA strands does not proceed to the ends thereof, so that the displaced strands remain attached to the template, forming a large web of interconnected strands.

When the nucleic acid polymerase is a RNA polymerase, the synthesized strands displaced from the template are RNA, and the cascade reaction produces a great number of single-stranded RNA molecules which hybridize to each other forming a large immobile network.

The synthesized RNA molecules will not be copied further by the RNA polymerase, but if further copies are desired, it is possible to proceed as follows: The produced network of hybridized RNA molecules is denatured, annealed to complementary oligonucleotides suitable as primers for cDNA synthesis and copied into cDNA strands by means of a reverse transcriptase, after which the cascade reaction proceeds further from the repeated oligonucleotide units of the cDNA strands.

Also in the cascade reaction it may be useful for purposes of monitoring the reaction or detecting the product or products that the nucleoside triphosphates present are labeled. Again, such label can for example be an enzyme, a radioactive isotope, a fluorescent compound, a chemiluminescent compound, a bioluminescent compound, a metal chelate or a hapten detectable by a specific secondary reaction.

An application aspect of the present invention provides a method of detecting a target molecule or group at a specific site, wherein a) a detector molecule that binds specifically to the target is attached to an oligonucleotide capable of taking part in a reaction to form a DNA template consisting of multiple tandem repetitions of said oligonucleotide, b) the oligonucleotide with attached detector molecule is contacted with the target site, and oligonucleotide with attached detector molecule not bound to target is removed, c) a reaction to form a DNA template consisting of multiple tandem repetitions of the oligonucleotide bound to the detector molecule is carried out, and d) the target is detected by detection of the bound amplified nucleic acid.

In this method it will often be expedient that further a cascade reaction as previously described is carried out before detecting the target.

In another embodiment of this method a) a detector molecule that binds specifically to the target is attached to a DNA template consisting of multiple tandem repetitions of an oligonucleotide unit, b) the template with attached detector molecule is contacted with the target site, and template with attached detector molecule not bound to target is removed, c) a cascade reaction as previously described is carried out, and d) the target is detected by detection of the bound amplified nucleic acid.

When the method comprises a cascade reaction, the presence of a large web of nucleic acid strands may be visible or detectable on its own, but usually the nucleoside triphosphates used in the process for producing the DNA template and, possibly, in the cascade reaction are labeled, and the target is detected by detecting the label.

The label on the labeled nucleoside triphosphates can for example be an enzyme, a radioactive isotope, a fluorescent compound, a chemiluminescent compound, a bioluminescent compound, a metal chelate or a hapten such as biotin detectable by a specific secondary reaction.

If the product of the detection reaction shall appear at a certain localization, the target molecules or groups to be detected should be bound to a specific site either before or after the reactions according to this invention take place. For example, they may be fixed to a solid surface, or they may be confined within a narrow space such as an organic cell.

A practical use of this aspect of the invention is the one wherein the target is a specific antigen, and the detector molecule is an antibody to said antigen. Another is the one wherein the target is a specific carbohydrate molecule or group, and the detector molecule is a lectin binding thereto. Yet another is the one wherein the target is a specific nucleic acid sequence, and the detector molecule is a DNA or RNA probe which hybridize specifically to the target sequence.

A further application aspect of the present invention provides a process for the amplification of a particular DNA fragment, wherein a first oligonucleotide is added to both ends of one copy of said DNA sequence and a second oligonucleotide complementary to the first one is added to both ends of another copy of said DNA sequence, and the resulting DNA sequences are copied stepwise by means of a template- and primer-dependent DNA polymarase in the presence of the necessary nucleoside triphosphates during repeated cycles of denaturation and annealing, the chain elongation taking place each time the annealing results in a frame-shifted hybridization giving rise to duplexes with buried 3' ends.

In another embodiment of this amplification process, a first oligonucleotide is added to the 5' end and a second oligonucleotide complementary to the first one is added to the 3' end of one copy of said DNA sequence and vice versa with another copy of said DNA sequence, and the resulting DNA sequences are copied stepwise by means of a template- and primer-dependent DNA polymerase in the presence of the necessary nucleoside triphosphates during repeated cycles of denaturation and annealing, the chain elongation taking place each time the annealing results in a frame-shifted hybridization giving rise to duplexes with buried 3' ends.

In yet another embodiment of this amplification process, at least one unit of an oligonucleotide showing dyad symmetry is added to both ends of said DNA sequence, and the resulting DNA sequence is copied stepwise by means of a template- and primer-dependent DNA polymerase in the presence of the necessary nucleoside triphosphates during repeated cycles of denaturation and annealing, the chain elongation taking place each time the annealing results in a frame-shifted hybridization giving rise to duplexes with buried 3' ends.

In each of the above three embodiments it may be expedient that the oligonucleotide units added to the ends of the particular DNA sequence are designed to contain restriction enzyme recognition sites bordering said DNA sequence.

In still another embodiment of the amplification process the particular DNA sequence to be amplified is either circularized or inserted into a circular oligonucleotide, and the resulting circular DNA is used as a template for an endless copying process by means of a nucleic acid polymerase capable of strand displacement and substantially without 5'-3' exonuclease activity in the presence of the necessary nucleoside triphosphates and, if necessary, a primer capable of binding to some portion of the oligonucleotide.

In this embodiment it may be expedient that the particular DNA sequence is inserted in a site of the circular oligonucleotide producing restriction enzyme recognition sites bordering said DNA sequence.

Each of the above described embodiments of the amplification process will produce by far the largest amplification when the process further comprises a cascade reaction as previously described.

Also in this amplification aspect of the invention it may be useful for monitoring or detection purposes that the nucleoside triphosphates used in the process are labeled.

BRIEF DESCRIPTION OF THE DRAWINGS

FIG. 1 illustrates the perfect match of two copies of one oligonucleotide comprising two units of dyad symmetry as well as the frameshifted annealing of the strands and DNA synthesis after the first denaturation of the double strand.

Similarly, FIG. 2 illustrates the perfect match of an oligonucleotide with internal repetitions and its complementary oligonucleotide as well as the frameshifted annealing of the two strands and DNA synthesis after the first denaturation of the double strand.

FIG. 3 illustrates the co-amplification of a DNA sequence of twelve "irrelevant" bases between two units of a dyad symmetry sequence.

FIG. 4 is a diagram illustrating an endless copying from a circular oligonucleotide. (1) is a linear oligonucleotide; (2) is the circularized oligonucleotide; (3) illustrates the copying of the circular oligonucleotide starting from a primer or a promoter at the 5' end; and (4) illustrates the strand displacement and continued copying after one turn of the oligonucleotide.

FIG. 6 illustrates the attachment of an oligonucleotide comprising repeated units of a dyad symmetry nucleotide sequence to an antibody which binds to a specific antigen fixed to a solid surface with a view to a subsequent multiplication and, optionally, cascade reaction to detect the antibody.

DETAILED DESCRIPTION OF THE INVENTION

Figure 5:
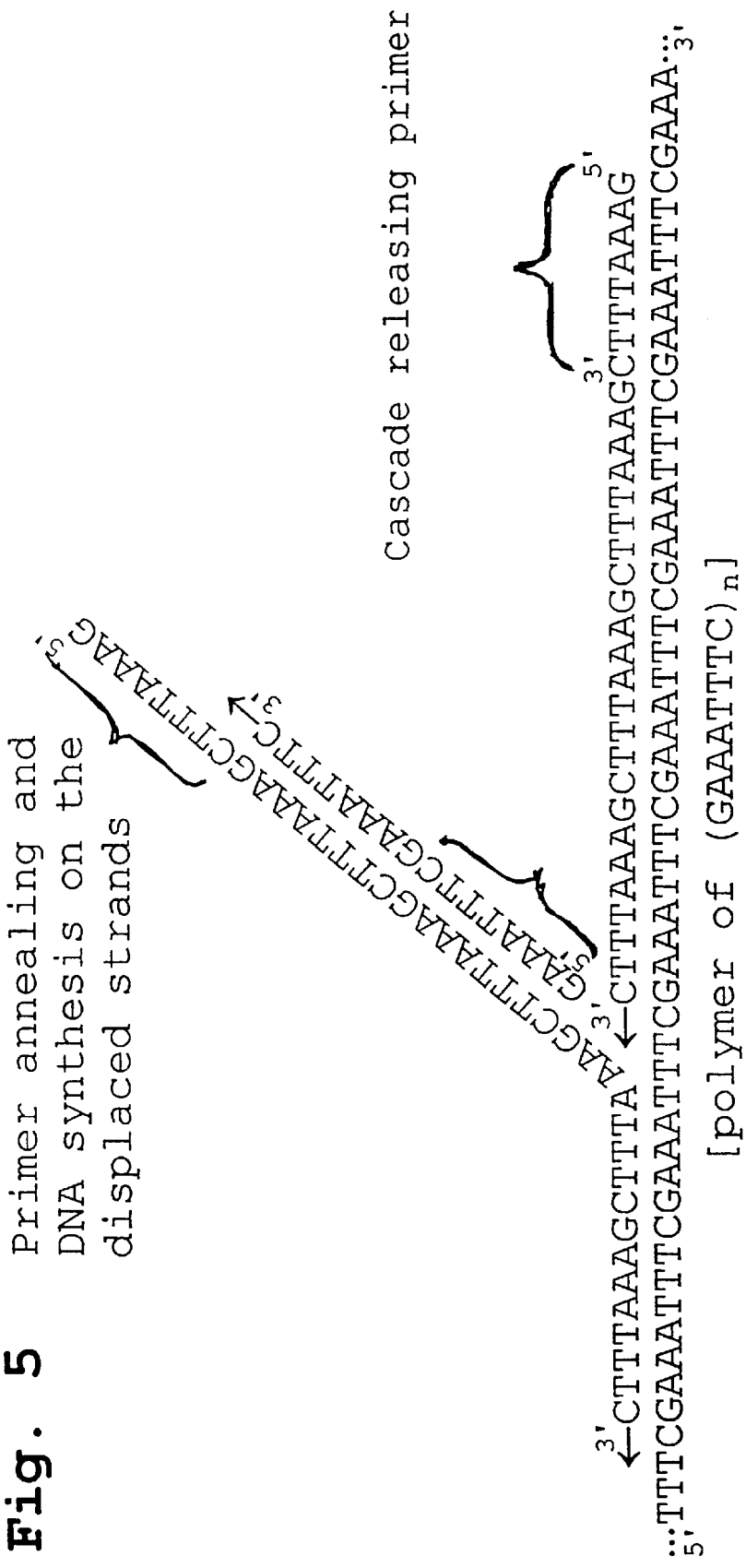
FIG. 5 illustrates a cascade amplification reaction from a DNA template consisting of multiple tandem repetitions of a dyad symmetry oligonucleotide unit using the dyad symmetry unit as a primer. The primer will hybridize to numerous complementary sequences in the template strand, and as the used DNA polymerase is capable of strand displacement and has no significant 5'-3' exonuclease activity, strand displacement will occur when the DNA synthesis reaches a site already occupied by a synthesized strand. Thus the DNA synthesis continues along the template strand, while more primer sequences bind to the displaced strands giving rise to the synthesis of new strands displacing each other.

The theoretically most productive embodiment of the invention is as follows:

i) The template is produced by polymerization from a dyad symmetry of a short repeating oligonucleotide unit to make it contain as many dyad symmetry sequences as possible.

ii) The cascade phase produces multiple DNA copies of the template. Due to the dyad symmetry nature of the sequence each of the multiple copies will have a sequence composition identical to that of the template and will thus be able to serve as template for the synthesis of multiple new copies that each can serve as a template for the synthesis of multiple new copies (and so on). (If the nucleic acid produced in the process is RNA, it would be necessary with the enzymes available today to convert this to DNA with a second enzyme (a reverse transcriptase) to make it a suitable template for new rounds of copying.)

This embodiment is described in greater detail in the following.

The DNA cascade is a two-phase reaction for the production of large amounts of DNA with a specific base sequence. In phase 1 multimers of a chosen oligonucleotide sequence are generated. In phase 2 this multimer structure (the template) is amplified to an amount several orders of magnitude larger than the amount of starting material. The linking of the two phases results in an effect far beyond what could be achieved with each of the two reactions individually. The DNA synthesized in phase 2 could serve as starting material for a second phase 1 or a second phase 2. The different steps can thus be repeated and combined according to the specific needs. In both phases several variants could be imagined. In the following an account of the principle of each stem will be given, along with a short mention of main variants and a presentation of possible applications.

Formation of Multimers

The multimer template formation by sequential growth from an oligonucleotide of dyad symmetry can be illustrated with the oligonucleotide GAAATTTCGAAATTTC (or (GAAATTTC)$_2$), (SEQ ID NO:3)

which is a direct repeat of the dyad symmetry GAAATTTC. Two molecules of this oligonucleotide can hybridize either with a perfect match or in a frameshifted position where only half of each molecule basepairs (FIG. 1). In the latter situation the duplexes will have either buried or free 3' ends, representing a frame shift either to the right or to the left. If a DNA polymerase and nucleoside triphosphates are present, buried 3' ends will be extended resulting in the growth of that DNA strand by half the size of the oligonucleotide employed. Thus, on the average 25% of the oligonucleotides will increase their length by 50%. If successive rounds of denaturation and annealing/chain elongation are performed, the molecules will keep increasing in size at a steadily increasing speed (There are two reasons why the rate of growth will increase. One is that a heterogeneous population of molecules is generated, which increases the frequency of frameshifting. The other is that as the molecules get longer, so do the possible frameshifts and thus the resulting growth.), until a level is reached where the reaction decreases in efficiency due to the fact that DNA polymerases can only synthesize some kilobases of DNA in vitro. By then our original 16mer has grown to a size of several kilobases.

A similar reaction could be obtained with two oligonucleotides having the sequence (GAAA)$_n$ and (TTTC)$_n$ (FIG. 2). Such a polymerization reaction from two oligonucleotides has previously been described by J. W. IJdo et al., loc. cit., and was shown to be able to generate 25 kilobase molecules from short oligonucleotides.

The principle as such should not be affected by the placing of an "irrelevant" πsequence between the initial copies of the growing oligonucleotide. (By "irrelevant" in this context is meant that the sequence on its own would be unable to engage in the reactions according to this invention). Thus, the oligonucleotide GAAATTTC["irrelevant" sequence]GAAATTTC should grow to generate the sequence (GAAATTTC["irrelevant" sequence])$_n$GAAATTTC (FIG. 3).

The advantage of adding the "irrelevant" sequence would be to have it co-amplified along with the amplifying oligonucleotide. The oligonucleotide would thus serve as carrier for the amplification of something else. The cost will of course be that as the size of the amplification unit increases, the number of copies in each polymer decreases since the total size of the polymer is fixed. The lower the number of units per polymer, the less DNA could be generated in the next phase where the maximum degree of amplification is primarily determined by the number of repeating units in each polymer.

In case of multimer template formation from a circular oligonucleotide, the multimer can be generated without repeated denaturation and annealing (FIG. 4). This requires the use of a polymerase capable of strand displacement and substantially without 5'-3' exonuclease activity as described for the cascade phase below and with kinetics identical to those described there. Also, the starting oligonucleotide should be bigger than is needed for multimer template formation from a linear molecule of dyad symmetry. However, the exact minimum size cannot be stated, as it will depend upon the sequence of the oligonucleotide and the size of the enzyme used to copy the circular DNA. The rigidity of the DNA depends upon the sequence of bases, and the more rigid it is, the longer the oligonucleotide needs to be in order to be bent into a circle. Furthermore, this circle must be big enough to enable the DNA polymerase to operate on it. If the original oligonucleotide is not big enough to fulfill these requirements, it can be elongated as described in the previous paragraph, until it has reached a sufficient size. Apart from the size requirements, the circularization variant only requires that the molecule to be circularized has a 5'-phosphate group and a 3'-hydroxy group as well as the addition of a DNA or RNA ligase under suitable reaction conditions including the presence of an energy-rich molecule like ATP to donate the necessary energy for the covalent linking of the ends. If the circular oligonucleotide has to be fixed at a certain site, it must be connected to a detector molecule, contain a detector molecule or contain a moiety capable of attaching to a detector molecule.

The possibility of forming a polymer from a circular template may be used to identify molecules capable of forming circles when complemented with a suitable template, or capable of serving as templates for circularization of the complementing DNA. The existence of a certain biological molecule can thus be detected through its ability to induce circularization of a linear DNA molecule added to it, and the circularization detected through the ability of a third DNA molecule to bind to the circle initiating rolling circle replication as described in the Toyobo patent, loc. cit.

However, the circularization may more conveniently be performed towards the 3'-end of the template, such that this end can serve as a primer for the rolling circle replication. Not only does this approach eliminate the need for the addition of an extra primer, it also keeps circles erroneously formed at cross reacting sites from being copied, unless they by chance coincide with a 3'-end. This approach also has the further advantage that the polymer would be covalently linked to the 3'-end which is detected. Thus, if the circle is formed at a site within a chromosome, the polymer will be a continuation of the chromosomal DNA at that site, and if the circle is formed on DNA captured in a microtitre well, on magnetic beads or otherwise, the polymer will be a continuation of the captured DNA. As a result of this, the polymer is not only specifically synthesized at the relevant site, but also very efficiently retained here.

The formation of the polymer can be directly detected if it is synthesized from labeled nucleotides, but more specificity and sensitivity would be obtained by adding a separate detection step, which could be a DNA cascade on the polymer, or possibly other approaches like PRINS or FISH. A prerequisite for this type of reaction is that the DNA studied has a suitably located 3'-end. If such an end is not naturally available, it may be generated artificially e.g. by digestion with a suitable restriction enzyme.

A further aspect of this assay is that it is not only sensitive to the sequence of the DNA template, but also to the form of it (broken (with a 3'-end) or continuous (no 3'-end)). It should thus be possible to determine not only if and where a certain target sequence is present, but also whether it is broken or not. Such breaks could result from a variety of enzymatic actions (e.g. topoisomerases) and pathological processes (e.g. chromosome breaks in cancer).

Reverting the setup of the assay, such that it is the DNA in the sample that is circularized on the DNA added, has the consequence that it is the DNA in the sample which is copied in the rolling circle replication. Consequently, the sequence composition of the DNA in the polymer will reflect that of the sample and a subsequent cascade reaction on the polymer can be released with primers inside the segments used for circularization, such that any "wrong" circle formed would be undetected, as it could not bind the cascade primers. Furthermore, the DNA synthesized in the cascade reaction would also correspond to the sample, and could on its own be used for analytical purposes (used as probe, sequenced etc.).

A circular oligonucleotide as described above can also be used directly as a template for the cascade phase below, if such is desired.

The Cascade Phase

If the original oligonucleotide is added to the polymers, it will bind at numerous positions along the elongated DNA, since what we have is a long polymer containing up to several thousand tandem copies of the original oligonucleotide. If the annealing occurs in the presence of labeled nucleotides and a DNA polymerase substantially without 5'-3' exonuclease activity, these hybridizations will result in a similar number of priming events each generating a labeled partial copy of the polymer. Since the DNA polymerase has no significant exonuclease activity, strand-displacement will occur when the DNA synthesis reaches a site already occupied by an oligonucleotide, thus making it possible to produce multiple copies of the same segment of the polymer (FIG. 5).

As seen in FIG. 5, the single-stranded DNA that is produced by the strand-displacement also has the potential to bind new oligonucleotides (which give rise to two new strands displacing each other). In principle this process could go on for ever (and at a steadily increasing speed, since the number of new single strands generated exceeds the number of strands used to generate them), generating at maximum $m^n$ molecules by n rounds of strand displacement from a polymer containing m copies of the amplifying oligonucleotide. In practice the reaction is likely to slow down after some time since the new strands will get shorter and shorter with each generation. However, from one polymer molecule containing a thousand copies of the original oligonucleotide (m=1000), $10^{16}$ new molecules will likely be produced, if the reaction is run to completion (n reaching maximum value).

If the size of the original oligonucleotide is increased by inclusion of an "irrelevant" sequence as mentioned above this will of course also be produced in large amounts, though the total amplification will be decreased, and with very long additions only a few hundred molecules may be generated from each polymer.

In this case the reactions could be repeated, either phase 2 alone using all the new strands as templates for a second cascade reaction, or the complete reaction letting the new strands elongate themselves prior to a new cascade step. Repeating the complete reaction p times would at maximum result in a $(m^n)^p$ fold amplification.

Other ways of enhancing the cascade reaction would be by pre-reacting the polymer with the cascade releasing oligonucleotide(s) for a while before the DNA polymerase is added, thus ensuring that all potential binding sites will be used in the first round of DNA synthesis, and use of a degradable primer as described in the Becton Dickinson and Boehringer Mannheim patents (loc. cit.), to obtain a multitude of priming events from each site, or a combination of these approaches.

Alternatively, the recognition site of a RNA polymerase like the T7 RNA polymerase could be included in the amplification unit and the enzyme added at the end of the reaction as cascade amplifier (the T7 RNA polymerase will upon binding generate up to 40 RNA copies of the DNA sequence next to the recognition sequence, so if the original unit is amplified 10 fold during the polymerization phase and another 100 fold during the cascade phase the total amplification would then be 10×100 ×40=4000 fold).

Promoter sequences can be polymerized as illustrated here with the promoter for the T7 RNA polymerase.

The cascade phase can not only be released with a primer-dependent polymerase, but also with a promoter-dependent. polymerase; and the nucleic acid produced may be RNA rather than DNA as illustrated here for the promoter-dependent RNA-producing enzyme T7 RNA polymerase. The sequence of the T7 promoter is

CCCTATAGTGAGTCGTATTA       (SEQ ID NO:13).

The shortest dyad symmetry constructed from this sequence is:

CCCTATAGTGAGTCGTATT:AATACGACTCA
       CTATAGGG       (SEQ ID NO:14)

(":" indicates the axis of symmetry). Oligonucleotides containing at least one and a half unit of this dyad symmetry could be polymerized into a double stranded polynucleotide, each strand having the sequence (CCCTATAGTGAGTCGTATTAATACGACTCA
       CTATAGGG)$_n$       (SEQ ID NO: 15).

If, for instance, "n" is 100, this means that each strand contains 100 potential binding sites for the T7 RNA polymerase. To obtain binding of the polymerase it is not necessary that the DNA strands are separated (denatured) by heat or otherwise. It is sufficient to add the polymerase and RNA precursors (nucleoside triphosphates) to the polymer according to one of the many protocols describing RNA synthesis from a T7 promoter. The polymerase will then bind at multiple sites along the DNA strand providing high speed multifocal RNA synthesis.

This type of reaction might be especially suited for applications where it is of particular importance that the nucleic acids produced in the reaction are very precisely retained at the site of synthesis (e.g. gene localization on metaphase chromosomes). The reason for this is that the single stranded RNA molecules produced are self-complementary, just as the DNA strands from which they are copied. Together with the high concentration and the low complexity of these molecules, this will cause the strands to hybridize to each other almost immediately, forming a network with a size and density that would make it unlikely to diffuse away from the site of synthesis. Theoretically, the network could reach such a size and density that it precipitated, which would leave it completely unable to move unless subjected to some mechanical force (like vigorous shaking).

The network formed could not bind the T7 RNA polymerase for the production of further RNA strands as this enzyme only binds to DNA. If such is desired, it is necessary to copy the RNA molecules into cDNA molecules. This can be done from nucleoside triphosphates by a reverse transcriptase and requires that the network is denatured (by heating or otherwise) and annealed to complementary oligonucleotides that can serve as starting points (primers) for the DNA synthesis.

Possible Applications

Amplifications without Added "Irrelevant" DNA

In this situation the oligonucleotide(s) only amplify itself (themselves). Since what is generated is only large amounts of the chosen short oligonucleotide and not some "biological" molecule, the reaction is particularly suited for detection purposes.

A prerequisite for this type of use is that the molecules can be brought to stay at a relevant site. Initially, this can be obtained by fixation of the polymer template for the cascade reaction to a detector molecule capable of binding specifically to the relevant site. This fixation may be obtained either by a chemical reaction between reactive groups on the two molecules or by an affinity reaction where the template contains a moiety that will bind specifically to the detector molecule. Thus, if the detector molecule is avidin or streptavidin, the template can be specifically attached thereto, if it contains a biotin moiety. Similarly, if the detector molecule is an antibody, the template can be attached specifically thereto, if it contains an antigen recognized by that antibody. This binding of the template may take place prior to, concurrently with or after the binding of the detector molecule to the relevant target. If preferable, an oligonucleotide capable of taking part in the formation of the polymer template may be attached instead of the template, and the template may then be formed at the detector molecule.

If the polymer formation starts from a circularized oligonucleotide, the circle can be used to cause the covalent binding of the polymer to the target detected, or serve as an anchoring point for the polymer, with the polymer ending in the circle and the circle encircling the target.

Once the template has been attached to the relevant site, the cascade reaction may be conducted. As can be deduced from FIG. 5, the strand displacement occurring in this phase will generate single-stranded molecules which are either attached directly or indirectly to the polymer template or are attached to other similar molecules in a large network which is unable to move around due to its size. The nucleic acids synthesized during the cascade phase will thus stay with the polymer that was attached to the relevant site. Depending upon the experimental setup this retention of the product can be enhanced by the characteristics of the relevant site. Thus, for instance, if the reaction is performed within a cell, the skeleton and membrane of the cell will serve to increase the retention of the product.

If the substrate for the nucleic acid synthesis is labeled nucleotides, the synthesized nucleic acids will be labeled. Thus, the $10^{16}$ molecules generated from one precursor molecule in the example above could be labeled. This number of labeled molecules is far above the detection limit in most laboratory reactions. Thus, if the initiating oligonucleotides are fixed to a specific detector molecule (like an antibody to an antigen of interest) the presence (binding) of this detector molecule could be visible even if only a single molecule is bound to the target (FIG. 6).

We would thus have a detection system with the highest possible sensitivity, since it could detect the existence of single entities. For most applications this level of sensitivity would be meaningless as it would be difficult to tell specific binding of single detector molecules from the unavoidable non-specific binding of these molecules. However, the high level of sensitivity would ensure that the sensitivity would always be sufficient.

It should be noted that the polymerization step is a non-specific reaction in the sense that any oligonucleotide with the ability to participate in such a reaction could do so under the right condition. Thus, a number of different oligonucleotides could be polymerized in one single reaction. By contrast, the cascade step is a specific step dependent on the addition of a specific oligonucleotide (or enzyme) to release the cascade. This could be utilized for differential staining of multiple targets. If a number of different oligonucleotides were attached to a corresponding number of antibodies and these were bound to their corresponding antigens, all the oligonucleotides could be polymerized in one single reaction. Subsequently, each polymer could be used as template for a specific cascade reaction released by the relevant oligonucleotide. Thus, if the first cascade was released with a red label, the second cascade with a green label and the third cascade with a blue label, the first target would appear in red, the second in green and the third in blue.

Co-Amplification of "Irrelevant" DNA

As described previously some other DNA sequence could be placed in the array of annealing DNA. This "irrelevant" DNA could in principle be of any type, as long as the size is not excessive, making the polymerization in phase 1 impossible. Thus, the DNA multiplication and, possibly, cascade could be used for the generation of large amounts of some interesting DNA sequence just as the polymerase chain reaction (PCR) and cloning. The DNA generated could then be used for whatever purposes DNA is used for. It could for instance be labeled during the synthesis and used as a hybridization probe, or it could be characterized by sequencing or otherwise.

To carry out the amplification of this DNA it is of course necessary to add the annealing sequences to the ends of the DNA of interest. This could be done in either of a number of ways. The sequences could be ligated directly to the ends of the DNA by standard ligation procedures, or it could be contained within a vector used for cloning of the DNA, for instance flanking the polylinker found in most modern vectors. Whatever method is chosen, the end result would be a DNA sequence capable of self-amplification through a DNA multiplication and cascade. If it is necessary to release the amplified "irrelevant" DNA from the amplifying sequences after the amplification, the annealing DNA may be designed to contain recognition sites for restriction enzymes.

If multiplication by means of two complementary oligonucleotide sequences is used, this may be done in two different ways. Either a first oligonucleotide, e.g. ATCG, may be added to both ends of one batch of the "irrelevant" DNA to be amplified, and a second oligonucleotide complementary to the first one, in casu CGAT, added to both ends of another batch of the "irrelevant" DNA, the resulting DNA sequences hybridizing and polymerizing as follows:

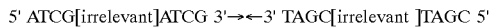

5' ATCG[irrelevant]ATCG 3'→←3' TAGC[irrelevant]TAGC 5'

Or the first oligonucleotide may be added to the 5' end and the second oligonucleotide to the 3' end of the first batch of "irrelevant" DNA, while the first oligonucleotide is added to the 3' end and the second oligonucleotide to the 5' end of the second batch of "irrelevant" DNA, the resulting DNA sequences hybridizing and polymerizing as follows:

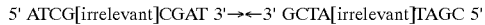

5' ATCG[irrelevant]CGAT 3'→←3' GCTA[irrelevant]TAGC 5'

If multiplication by means of one oligonucleotide showing dyad symmetry is used, this dyad symmetry oligonucleotide, e.g. GAAATTTC, is added to both ends of the "irrelevant" DNA, the resulting DNA sequence hybridizing and polymerizing as follows:

5' GAAATTTC[irrelevant]GAAATTTC 3'→←3' CTTTAAAG[irrelevant]CTTTAAAG 5'

In these embodiments of the multiplication reaction the first step of hybridization and polymerization will produce complementary copies of the "irrelevant" DNA; the second step will produce actual copies of the "irrelevant" DNA and so forth. The result will be a template comprising shifting actual and complementary copies of the desired DNA. A subsequent cascade reaction copying both the resulting template and the copies of the template will thus produce a multitude of both actual and complementary copies of the desired DNA.

On the other hand, if the multiplication reaction is carried out by endless copying of a circular DNA incorporating the "irrelevant" DNA, the resulting template will comprise multiple complementary DNA or RNA copies of the desired DNA. If the template is DNA, a subsequent cascade reaction will in the first instance produce actual copies of the desired DNA, in the next instance complementary copies thereof and so forth. If the template is RNA, this may by reverse transcription be copied into cDNA comprising actual copies of the desired DNA, and a subsequent cascade reaction will in the first instance produce complementary copies of the desired DNA, in the next instance actual copies thereof and so forth. In every case the end result will be a multitude of both actual and complementary copies of the desired DNA.

Co-amplification reactions could of course also be used for detection purposes by labeling as described previously. The amount of DNA generated in the cascade step would be much lower, but this may be affordable. Also, the larger size of the amplification unit might increase the retention at the site of synthesis compensating for the lower overall yield.

Furthermore, with the co-amplification of some other DNA it would be possible to release the cascade with an oligonucleotide primer hybridizing to some sequence within this DNA rather than to the oligonucleotide sequence used for the polymerization. This would likely increase the specificity of the reaction further.

Similarly, the detector molecule could be present as an "irrelevant" sequence directing the amplifying construct to a site capable of hybridizing with the "irrelevant" sequence thus binding the cascade reaction to that site.

EXAMPLES

Example 1

Formation of a Polymer From a Tandem Repeat of a dyad Symmetry Sequence.

The sequence

5'-ACAAATTTGT-3'                    (SEQ ID NO:16)

has a dyad symmetry. The oligonucleotide

5'-ACAAATTTGTACAAATTTGT-3'          (SEQ ID NO: 17)

contains two repeats of this dyad symmetry and can be elongated to an apparent size of about 20 kb (as estimated by neutral agarose gel electrophoresis) by the reaction described here. In this example the resulting polymer is labeled with digoxigenin, as digoxigenin-labeled dUTP is added to the reaction. The digoxigenin-dUTP can of course be omitted or replaced with dTTP.

A similar elongation is achieved if the oligonucleotide is synthesized with a biotin molecule attached to the 5'-end, making it possible to fix the oligonucleotide or its polymer to avidin, if such is desired.

The 10 μl taken out each ten cycles can be used to monitor the progress of the polymer formation. It appears that most of the elongation occurs in the last incubation, as predicted from the theoretical considerations. It also appears that the polymers vary more in size as they become longer, which is also as expected.

Procedure

Mix the following in a final volume of 20 μl:

1–10 ng (about 1 pmol) oligonucleotide

2 μl glycerol

2 μl 10×Taq-buffer (supplied by the supplier of Taq polymerase)

2 nmol each of dATP, dCTP, dGTP and dTTP 500 pmol dig-11-dUTP (Boehringer Mannheim)

2U Taq polymerase (Boehringer Mannheim)
Water to 20 µl
　Incubate in a thermocycler for 10 cycles at:
　30° C. for 2 minutes
　50° C. for 1 minute
　70° C. for 1 minute.
　Then transfer 10 µl of the mixture to a new reaction and
add the following mixture:
1 µl glycerol
1 µl 10 ×Taq-buffer
2 nmol each of dATP, dCTP, dGTP and dCTP
500 pmol dig-11-dUTP
2 U Tag polymerase
Water to 10 µl.
　Incubate in a thermocycler for 10 cycles at:
　40° C. for 2 minutes
　65° C. for 2 minutes
　90° C. for 1 minute.
　Then transfer 10 µl of the mixture to a new reaction and
add the following mixture:
1 µl glycerol
1 µl 10×Taq-buffer
2 nmol each of dCTP, dGTP, dTTP
4 nmol dATP
500 pmol dig-11-dUTP
4 U Taq polymerase
Water to 10 µl.
　Incubate in a thermocycler for 10 cycles at:
　50° C. for 2 minutes
　70° C. for 10 minutes
　90° C. for 1 minute.
　After this the polymer had reached a size of about 20 kb in the experiments recited here. Repeating the last incubation twice did not result in any further apparent increase in polymer size.

Example 2

The gene mutated in Cystic Fibrosis can be stained in preparations of metaphase chromosomes and interphase nuclei In this protocol an oligonucleotide probe is circularized and ligated on the normal variant of the Cystic Fibrosis gene in a preparation of fixed cells from a healthy human donor. After ligation a second primer is added. This primer hybridizes to the part of the circle not hybridizing with the genomic DNA and initiates polymer formation through rolling circle replication of the circle. After this the same primer is added again, but this time together with a non-complementary primer capable of hybridizing with the polymer. Together these two primers then generate a cascade reaction on the polymer. With the inclusion of digoxigenin-labeled dUTP in the reaction mixture, this cascade reaction can subsequently be made visible by incubation with fluorochrome-labeled antidigoxigenin antibody.

At sites where all reactions work optimally the stamina in metaphase chromosomes looks like a little down, situated in the middle of the long arm of chromosome 7. However, none of the steps works to 100% in all cells, so the appearance will vary from cell to cell. If the first oligonucleotide does not hybridize to the target sequence or if it is not ligated after hybridization, no staining can be generated. The same is the case if the hybridization of the polymer-generating oligonucleotide or the rolling circle replication fails. Where all of these reactions have worked, the cascade can be released. The amount of (labeled) DNA made in these reactions is expected to vary depending on how much the individual polymers increased in the preceding step (the longer the polymer, the more cascade product) and depending on spatial conditions at the individual site (how much DNA can be accomodated). In accordance with this the appearance of individual chromosomes 7 after the reaction varies from no signal to a dot-like signal to a down-like signal; and of the two chromosomes 7 in a single metaphase none, one or both may be stained.

Most interphase nuclei also contain stained sites. However, since the nuclei, unlike the chromosomes, present no morphological features to help determine if the staining is located at the right site, this result is more difficult to interpret.

Procedure

Make a fresh spreading of cells fixed in methanol and acetic acid (3:1) on a microscope slide. To facilitate access to the hybridization sites, it is important that the chromosomes are well spread and not embedded in dense cytoplasm.

Prepare the following mixture for hybridization and ligation of the Cystic Fibrosis probe:

2.5 pmol probe (5'-p-
　　AAGATGATA(T)$_4$CTTTAATG(T)$_{16}$ATAATGTTAA
　　GTGACCGGCAGC(A)$_4$TG(T)$_{16}$CATCATAGGAAACACCA-
　　3')　　　　　　　　　　　　　　　　　　　(SEQ ID NO:18)

5 µl 10×Tth ligase buffer (1×buffer: 20 mM Tris.HCl pH 9.0, 100 mM KCl 10 mM MgCl$_2$, 1 mM EDTA and 0.1% "Triton® X-100")
10 µl 10 mM NAD
5 µg sonicated and denatured salmon sperm DNA
5 µg BSA
5 µl glycerol
12.5 U Tth DNA ligase
water to 50 µl.

Add the mixture to the slide and spread with a coverslip. Incubate at 92.5° C. for 2.5 minutes (to denature the genomic DNA) and then at 55° C. for 30 minutes (to hybridize and ligate probe).

Then wash in 30% formamide, 2×SSC pH 7.0 (1×SSC: 150 mM NaCl, 15 mM sodium citrate) at 42° C. for 10 minutes and in 2×SSC at 55° C. for 10 minutes to remove both free and unligated probes.

Dehydrate the slide in an ethanol series (70–90–99%) and air dry it.

The slide is now ready for polymer formation.

To perform this, mix the following:
1 pmol primer (5'-TGCTGCCGGTCACTTAACAT-3')　　　　(SEQ ID NO:19)

5 nmol each of dATP, dCTP, dGTP and dTTP
5 µg BSA
5 µl 10×Φ-29 buffer (1×Φ-29 buffer: 50 mM Tris.HCl pH 7.5, 10 mM MgCl$_2$, 20 mM (NH$_4$)$_2$SO$_4$, 1 mM DTT)
340 ng Φ-29 DNA polymerase
water to 50 µl Add the mixture to the slide, spread with a coverslip and incubate at 30° C. for 1 hour.

Transfer the slide to washing buffer (4×SSC, 0.05% Tween®-20) and wash for 5 minutes at ambient temperature.

Dehydrate the slide in an ethanol series (70–90–99%) and air dry it.

The slide is now ready for the cascade reaction.

To perform the cascade reaction, mix the following reagents:

4 pmol of the primer used to generate the polymer
4 pmol of a primer complementary to the polymer (in this case:

5'-AAGATGATATTTTCTTTAATG-3')  (SEQ ID NO: 20)

5 nmol each of dATP, dCTP and dGTP
4 nmol dTTP
1 nmol digoxigenin dUTP
5 μl glycerol
5 μl 10×Φ-29 buffer
340 ng Φ-29 DNA polymerase
water to 50 μl.

Add the mixture to the slide, spread with a coverslip and incubate at 37° C. for 1 hour. Transfer the slide to washing buffer and equilibrate in this buffer for 5 minutes.

Then add 100 μl fluorescein-labeled anti-digoxigenin antibody to visualize the digoxigenin-labeled DNA synthesized in situ (spread with a coverslip). The antibody should be in washing buffer supplemented with 5% non-fat dry milk. Incubate for 30 minutes at ambient temperature to 37° C. and away from light. Wash the slide 3×5 minutes in washing buffer at ambient temperature.

The slide is now ready to be analyzed.

What is claimed is:

1. A method for amplifying a linear nucleic acid, which process comprises:
   (a) hybridizing ends of the linear nucleic acid to a chromosomal locus so that the linear nucleic acid is circularized; and
   (b) contacting the circularized nucleic acid with a polymerase capable of strand displacement and with nucleoside triphosphates, so that a 3'-end of the chromosomal locus serves as a primer for rolling circle replication of the circularized nucleic acid, and wherein copies of the linear nucleic acid are produced by said rolling circle replication.

2. A method according to claim 1 in which the chromosomal locus is detected by detecting the amplified nucleic acid.

3. A method according to claim 1 in which the nucleoside triphosphates are labeled.

4. A method according to claim 3 in which the label is selected from the group consisting of: an enzyme, a radioactive isotope, a fluorescent compound, a chemiluminescent compound, a bioluminescent compound, a metal chelate, and a hapten.

5. A method according to claim 1 in which the polymerase is without 5'-3' exonuclease activity.

6. A method according to claim 1 wherein:
   (i) the product of the rolling circle replication contains multiple tandem repeat copies of the linear nucleic acid sequence; and
   (ii) said product is further amplified in a cascade reaction that comprises contacting the product with the polymerase in the presence of nucleoside triphosphates and a primer, so that nucleic acid synthesis is initiated at the tandem repeats.

7. A method according to claim 6 in which the linear nucleic acid comprises a sequence having dyad symmetry.

8. A method according to claim 7 in which the sequence having dyad symmetry is the primer for nucleic acid synthesis in the cascade reaction.

9. A method according to claim 6 in which the nucleoside triphosphates are labeled.

10. A method according to claim 9 in which the label is selected from the group consisting of: an enzyme, a radioactive isotope, a fluorescent compound, a chemiluminescent compound, a bioluminescent compound, a metal chelate, and a hapten.

11. A method according to claim 6 which the polymerase is without 5'-3' exonuclease activity.

12. A method for amplifying a linear nucleic acid, which process comprises:
   (a) hybridizing ends of the linear nucleic acid to a nucleic acid template so that the linear nucleic acid is circularized, said nucleic acid template being fixed to a solid support; and
   (b) contacting the circularized nucleic acid with a polymer capable of strand displacement and with nucleoside triphosphates, so that a 3'-end of the nucleic acid template serves as a primer for rolling circle replication of the circularized nucleic acid, and wherein the linear nucleic acid is amplified by said rolling circle replication.

13. A method according to claim 12 in which the nucleic acid template is detected by detecting the amplified nucleic acid.

14. A method according to claim 12 in which the nucleoside triphosphates are labeled.

15. A method according to claim 14 in which the label is selected from the group consisting of: an enzyme, a radioactive isotope, a fluorescent compound, a chemiluminescent compound, a bioluminescent compound, a metal chelate, and a hapten.

16. A method according to claim 12 in which the polymerase is without 5'-3' exonuclease activity.

17. A method according to claim 12 wherein:
   (i) the product of the rolling circle replication contains multiple tandem repeat copies of the linear nucleic acid sequence; and
   (ii) said product is further amplified in a cascade reaction that comprises contacting the product with the polymerase in the presence of nucleoside triphosphates and a primer, so that nucleic acid synthesis is initiated at the tandem repeats.

18. A method according to claim 17 in which the linear nucleic acid comprises a sequence having dyad symmetry.

19. A method according to claim 18 in which the sequence having dyad symmetry is the primer for nucleic acid synthesis in the cascade reaction.

20. A method according to claim 17 in which the nucleoside triphosphates are labeled.

21. A method according to claim 20 in which the label is selected from the group consisting of: an enzyme, a radioactive isotope, a fluorescent compound, a chemiluminescent compound, a bioluminescent compound, a metal chelate, and a hapten.

22. A method according to claim 17 in which the polymerase is without 5'-3' exonuclease activity.

* * * * *

SEQUENCE LISTING

<160> NUMBER OF SEQ ID NOS: 22

<210> SEQ ID NO 1
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 1
ttagggttag ggttagggtt agggttaggg   30

<210> SEQ ID NO 2
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 2
ccctaaccct aaccctaacc ctaaccctaa   30

<210> SEQ ID NO 3
<211> LENGTH: 16
<212> TYPE: DNA
<213> ORGANISM: Artificial Sequence
<220> FEATURE:
<223> OTHER INFORMATION: oligonucleotide primer

<400> SEQUENCE: 3
gaaatttcga aatttc   16

<210> SEQ ID NO 4
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 4
gaaatttcga aatttcgaaa tttc   24

<210> SEQ ID NO 5
<211> LENGTH: 20
<212> TYPE: DNA
<213> ORGANISM: Artificial Sequence
<220> FEATURE:
<223> OTHER INFORMATION: oligonucleotide

<400> SEQUENCE: 5
gaaagaaaga aagaaagaaa   20

```
<210> SEQ ID NO 6
<211> LENGTH: 20
<212> TYPE: DNA
<213> ORGANISM: Artificial Sequence
<220> FEATURE:
<223> OTHER INFORMATION: oligonucleotide

<400> SEQUENCE: 6
tttctttctt tctttctttc                                              20

<210> SEQ ID NO 7
<211> LENGTH: 28
<212> TYPE: DNA
<213> ORGANISM: Artificial Sequence
<220> FEATURE:
<223> OTHER INFORMATION: oligonucleotide

<400> SEQUENCE: 7
gaaagaaaga aagaaagaaa gaaagaaa                                     28

<210> SEQ ID NO 8
<211> LENGTH: 28
<212> TYPE: DNA
<213> ORGANISM: Artificial Sequence
<220> FEATURE:
<223> OTHER INFORMATION: oligonucleotide

<400> SEQUENCE: 8
tttctttctt tctttctttc tttctttc                                     28

<210> SEQ ID NO 9
<211> LENGTH: 28
<212> TYPE: DNA
<213> ORGANISM: Artificial Sequence
<220> FEATURE:
<223> OTHER INFORMATION: amplified oligonucleotide with amplification
      of 12 units of irrelevant sequence between units of sequence
      with dyad symmetry
<220> FEATURE:
<221> NAME/KEY: misc_feature
<222> LOCATION: (1)..(28)
<223> OTHER INFORMATION: where n can be a or t or g or c or unknown

<400> SEQUENCE: 9
gaaatttcnn nnnnnnnnnn gaaatttc                                     28

<210> SEQ ID NO 10
<211> LENGTH: 48
<212> TYPE: DNA
<213> ORGANISM: Artificial Sequence
<220> FEATURE:
<223> OTHER INFORMATION: amplified oligonucleotide with amplification
      of 12 units of irrelevant sequence between units of sequence
      with dyad symmetry
<220> FEATURE:
<221> NAME/KEY: misc_feature
<222> LOCATION: (1)..(48)
<223> OTHER INFORMATION: where n may be a or t or g or c or unknown

<400> SEQUENCE: 10
gaaatttcnn nnnnnnnnnn gaaatttcnn nnnnnnnnnn gaaatttc               48

<210> SEQ ID NO 11
<211> LENGTH: 32
<212> TYPE: DNA
<213> ORGANISM: Artificial Sequence
<220> FEATURE:
```

```
<223> OTHER INFORMATION: oligonucleotide primer

<400> SEQUENCE: 11
gaaatttcga aatttcgaaa tttcgaaatt tc                          32

<210> SEQ ID NO 12
<211> LENGTH: 56
<212> TYPE: DNA
<213> ORGANISM: Artificial Sequence
<220> FEATURE:
<223> OTHER INFORMATION: oligonucleotide

<400> SEQUENCE: 12
tttcgaaatt tcgaaatttc gaaatttcga aatttcgaaa tttcgaaatt tcgaaa    56

<210> SEQ ID NO 13
<211> LENGTH: 19
<212> TYPE: DNA
<213> ORGANISM: Artificial Sequence
<220> FEATURE:
<223> OTHER INFORMATION: T7 promoter

<400> SEQUENCE: 13
ccctatagtg agtcgtatt                                         19

<210> SEQ ID NO 14
<211> LENGTH: 19
<212> TYPE: DNA
<213> ORGANISM: Artificial Sequence
<220> FEATURE:
<223> OTHER INFORMATION: dyad symmetry of T7 promoter

<400> SEQUENCE: 14
aatacgactc actataggg                                         19

<210> SEQ ID NO 15
<211> LENGTH: 38
<212> TYPE: DNA
<213> ORGANISM: Artificial Sequence
<220> FEATURE:
<223> OTHER INFORMATION: oligonucleotide

<400> SEQUENCE: 15
ccctatagtg agtcgtatta atacgactca ctataggg                    38

<210> SEQ ID NO 16
<211> LENGTH: 10
<212> TYPE: DNA
<213> ORGANISM: Artificial Sequence
<220> FEATURE:
<223> OTHER INFORMATION: oligonucleotide

<400> SEQUENCE: 16
acaaatttgt                                                   10

<210> SEQ ID NO 17
<211> LENGTH: 20
<212> TYPE: DNA
<213> ORGANISM: Artificial Sequence
<220> FEATURE:
<223> OTHER INFORMATION: oligonucleotide

<400> SEQUENCE: 17
acaaatttgt acaaatttgt                                        20
```

```
<210> SEQ ID NO 18
<211> LENGTH: 92
<212> TYPE: DNA
<213> ORGANISM: Artificial Sequence
<220> FEATURE:
<223> OTHER INFORMATION: Cystic Fibrosis probe

<400> SEQUENCE: 18
aagatgatat tttctttaat gtttttttt tataatgtta agtgaccggc agcaaaatgt      60
tttttttttt tttttcatca taggaaacac ca                                  92

<210> SEQ ID NO 19
<211> LENGTH: 20
<212> TYPE: DNA
<213> ORGANISM: Artificial Sequence
<220> FEATURE:
<223> OTHER INFORMATION: polymer primer

<400> SEQUENCE: 19
tgctgccggt cacttaacat                                                20

<210> SEQ ID NO 20
<211> LENGTH: 21
<212> TYPE: DNA
<213> ORGANISM: Artificial Sequence
<220> FEATURE:
<223> OTHER INFORMATION: primer complementary to the polymer

<400> SEQUENCE: 20
aagatgatat tttctttaat g                                              21

<210> SEQ ID NO 21
<211> LENGTH: 40
<212> TYPE: DNA
<213> ORGANISM: Artificial Sequence
<220> FEATURE:
<223> OTHER INFORMATION: oligonucleotide

<400> SEQUENCE: 21
gaaatttcga aatttcgaaa tttcgaaatt tcgaaatttc                          40

<210> SEQ ID NO 22
<211> LENGTH: 12
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (1)..(12)
<223> OTHER INFORMATION: where n may be a or t or g or c or unknown

<400> SEQUENCE: 22
nnnnnnnnnn nn                                                        12
```